(12) United States Patent
Saito et al.

(10) Patent No.: US 7,621,935 B2
(45) Date of Patent: Nov. 24, 2009

(54) WIRE FOR INSERTING INTO BIOLOGICAL DUCT

(75) Inventors: Satoshi Saito, Tokyo (JP); Daisuke Kawabe, Tokyo (JP)

(73) Assignee: Nihon University, Tokyo (JP)

( * ) Notice: Subject to any disclaimer, the term of this patent is extended or adjusted under 35 U.S.C. 154(b) by 11 days.

(21) Appl. No.: 10/549,529

(22) PCT Filed: Oct. 8, 2003

(86) PCT No.: PCT/JP03/12921

§ 371 (c)(1),
(2), (4) Date: Sep. 16, 2005

(87) PCT Pub. No.: WO2004/084739

PCT Pub. Date: Oct. 7, 2004

(65) Prior Publication Data

US 2006/0173489 A1    Aug. 3, 2006

(30) Foreign Application Priority Data

Mar. 27, 2003 (JP) ............................. 2003-088981

(51) Int. Cl.
*A61M 29/00* (2006.01)
(52) U.S. Cl. .................................... 606/200

(58) Field of Classification Search ............... 606/200, 606/191, 198, 113, 114, 127, 159
See application file for complete search history.

(56) References Cited

U.S. PATENT DOCUMENTS

| 4,768,505 A | 9/1988 | Okada et al. ............... 128/328 |
| 6,066,158 A | 5/2000 | Engelson et al. ............ 606/200 |
| 6,336,934 B1 * | 1/2002 | Gilson et al. ............... 606/200 |
| 6,375,670 B1 * | 4/2002 | Greenhalgh ................ 606/200 |
| 6,432,122 B1 | 8/2002 | Gilson et al. |
| 6,716,231 B1 * | 4/2004 | Rafiee et al. ............... 606/200 |

FOREIGN PATENT DOCUMENTS

| JP | 2001-212152 | 8/2001 |
| JP | 2002-159503 A | 6/2002 |
| WO | WO99/56801 A2 | 11/1999 |

* cited by examiner

*Primary Examiner*—Kevin T Truong
(74) *Attorney, Agent, or Firm*—Young Basile

(57) ABSTRACT

A wire for insertion into intravital tracts applicable even to small-diameter tracts while securing the stream in the tract is to be provided. A capture filter 2 is disposed at the tip of a principal wire 1 consisting of steel filaments. The capture filter 2 is configured of four support wires 3 and a basket-shaped filter body 4 consisting of a meshed material. The filaments constituting the support wires 3 and those constituting the filter body 4 are integrally formed and consist of a superelastic alloy.

6 Claims, 3 Drawing Sheets

FIG. 3

| EXPANSIBLE DIAMETER (mm) | MESH SIZE (mm) |
|---|---|
| 8 | 0.34 |
| 7 | 0.31 |
| 6 | 0.26 |
| 5 | 0.22 |
| 4 | 0.17 |
| 3 | 0.13 |
| 2 | 0.09 |
| 1 | 0.04 |

WIRE FOR INSERTING INTO BIOLOGICAL DUCT

TECHNICAL FIELD

The present invention relates to a wire for insertion into intravital tracts provided with a capture filter to be temporarily arranged in an intravital tract, such as a blood vessel, to capture embolic material or the like in the tract.

BACKGROUND ART

In many cases of treating a lesion in an intravital tract, such as removing cholesterol or anything else that has accumulated in a blood vessel or removing gallstones in the gall duct, the substance concerned is removed from the wall surface of the tract. Where a blood vessel is to be so treated, these pieces of the removed substance will be carried by the blood flow and may block thinner blood vessels downstream.

According to a technique to address this problem disclosed in JP2001-212152A (hereinafter referred to as Patent Reference 1), a filter is temporarily arranged in the tract by inserting a wire provided with a capture filter, and such potentially embolic material is captured by the filter.

The capture filter according to Patent Reference 1 comprises a cage body composed by joining three or more linear alloy wires with one another at both front and rear ends and swelling midway parts of the plurality of alloy wires in the radial direction to arrange them along a substantially football-shaped border face, and an umbrella-shaped cover is formed by covering with an elastic membrane the part of the outer surface of that cage body, for instance, from the front end to substantially the middle point; embolic material is captured by that umbrella-shaped cover.

The wire is inserted into a leading catheter, and the capture filter in a state of being kept folded is inserted together with the leading catheter into a blood vessel. When they reach the target region, the front end of the wire is fed out forward from the leading catheter to let out the capture filter from the leading catheter into the aforementioned shape of swelling in the radial direction.

However, in the wire for insertion into intravital tracts, as the umbrella-shaped cover consisting of a membrane constitute the filter to capture embolic material, there is a fear that the umbrella-shaped cover itself may obstruct blood circulation in the blood vessel. There is a version in which many holes are bored in that membrane, but this still involves a fear of failure to ensure a sufficient blood stream.

Further, to consider a state in which capture filter is folded, the diameter of the capture filter will be increased by the thickness of the membrane doubled by the folding, and the filter will become correspondingly less adaptive to thin tracts.

An object of the present invention, attempted in view of these problems, is to provide a wire for insertion into intravital tracts whose diameter can be reduced without sacrificing the smoothness of the stream within the tract.

DISCLOSURE OF THE INVENTION

In order to solve the problems noted above, a wire for insertion into intravital tracts according to the aspect of the present invention uses as a principal wire flexible filaments to be inserted into an intravital tract, the tip of that principal wire being provided with a capture filter, the wire for insertion into intravital tracts being characterized in that the capture filter comprises a filter body consisting of a plurality of support wires all of whose nearer ends are spliced to the principal wire and radially extending in the direction toward the farther end and in the direction toward the outer diameter and a meshed material linked to the plurality of support wires and knit in such a shape that the face toward the support wires form a concave, the ends of the plurality of filaments knitted into a mesh form to constitute the filter body are divided into a plurality of sets, and the ends of filaments of each set are twined to form each of the support wires, and the filaments constituting the plurality of support wires and filter body have an elastic force to form the shapes.

According to the invention, by configuring the filter body of a meshed material, obstruction of the stream within the intravital tract is avoided.

Also, since it can be folded correspondingly smaller to the absence of the membrane unlike in the conventional one, it can be applied to tracts thinner in diameter.

Furthermore, the presence of the elastic force to form the aforementioned shape, no other mechanism to achieve swelling into the intended shape is needed, and the configuration is correspondingly simplified to make possible more compact folding.

Also, filaments constituting the support wires and filaments constituting the filter body are integrated to dispense processing to separately join the support wires and the filter body, with the result that no swollen nodal part is formed in any of the joined portions, making possible folding to a correspondingly thinner diameter.

Next, according to another aspect of the invention the mesh size of the meshed material decreases toward the central part of the concave, which is the farther end direction.

Since the stream of fluid in a tract is the highest in flow rate in the central part of the tract, embolic material floating in the fluid is captured, first from the concave central position of the filter body consisting of a meshed material. Therefore, by setting the meshes of the concave central position of the filter body smaller than anywhere else as according to the invention under the present application, the stream of the fluid can be more easily ensured by the meshes of the outer circumference of the filter while securely capturing small pieces of embolic material.

Since the meshes of the meshed material here are so inclined as to flatly lie relative to the stream of the fluid, more so toward the outer circumference whether the mesh openings are larger in relative terms, the aperture is equal to finer meshes in relative terms in a sectional view orthogonal to the stream of the fluid.

Next, according to another aspect of the invention, the filaments constituting the plurality of support wires and the filter body consist of a shape-memory alloy.

The composition using a shape-memory alloy makes more secure restorability of the originally intended shape even after staying in a folded state for a long time.

More preferably, it should be a superelastic alloy out of shape-memory alloys.

Next, according to a further aspect of the invention, there is provided with a guide wire joined to the convex side of the filter body and extending in the farther end direction.

The presence of the guide wire facilitates guidance of the capture filter swelling in the radial direction along the intravital tract.

Incidentally, it is preferable for the guide wire to be more flexible in the radial direction than the principal wire. While the principal wire is required to be just sufficiently rigid to permit feeding in the axial direction, it is preferable for the guide wire to have flexibility to permit trackability in the extending direction of the tract.

Next, according to another aspect of the invention, the central part of said filter body is joined to the nearer end side of a first tubular piece and fixed to the first tubular piece in a state in which the nearer end of said guide wire is inserted into the farther side of that first tubular piece.

Next, according to the aspect of the invention, the nearer ends of the plurality of support wires are all fixed to a second tubular piece in a state in which they are inserted into the farther side of the second tubular piece, and fixed to the second tubular piece in a state in which the tip of the principal wire is inserted into the nearer side of said second tubular piece.

BRIEF DESCRIPTION OF THE DRAWINGS

FIG. 3 is a drawing representing data of an embodiment.

BEST MODES FOR CARRYING OUT THE INVENTION

The present invention will be described in more detail with reference to the accompanying drawings.

Figure 1:
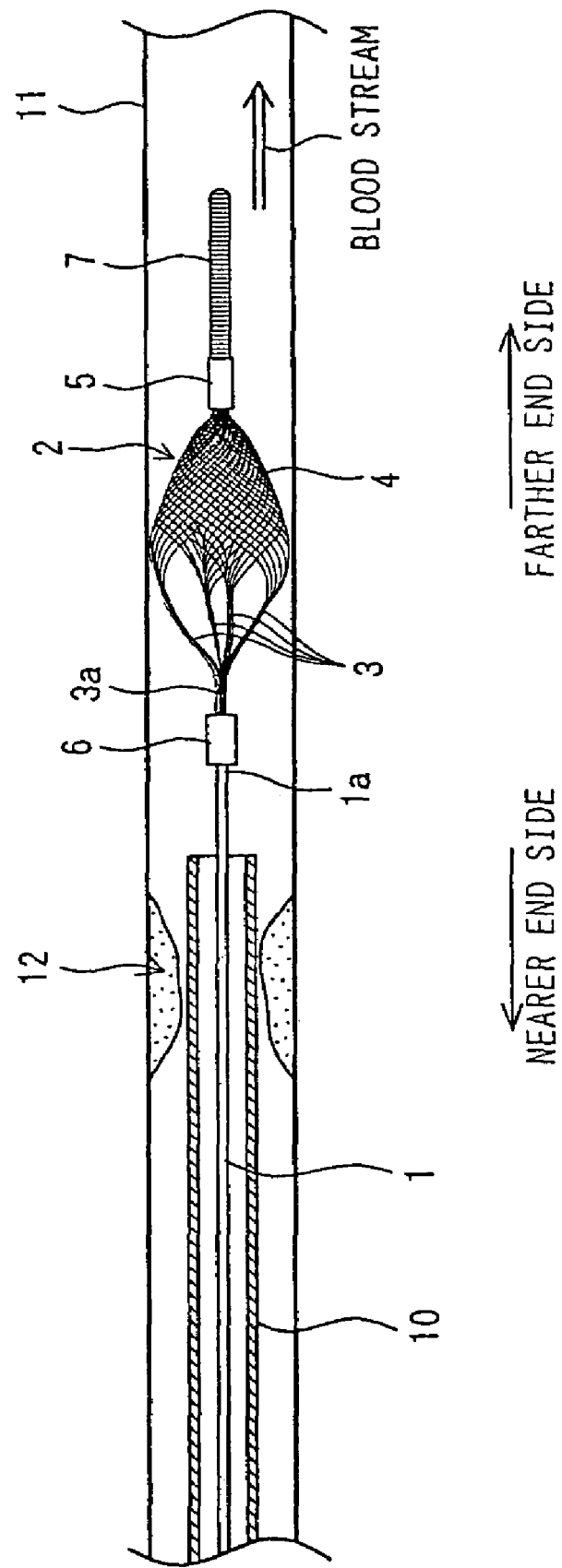
FIG. 1 is a drawing showing a wire for insertion into intravital tracts pertaining to a mode for carrying out the present invention.

FIG. 1 is a drawing showing a wire for insertion into intravital tracts in this mode for implementation and the state of its use. This FIG. 1 is a drawing of a state of insertion into a lesioned position in a blood vessel, which is one of intravital tracts.

As shown in FIG. 1, a capture filter 2 is disposed at the tip of a principal wire 1 consisting of steel filaments.

The capture filter 2 is configured of four support wires 3 and a basket-shaped filter body 4 consisting of a meshed material, concave toward the nearer position (convex toward the farther position).

The four support wires 3 are joined into one by twining their respective nearer ends 3a together. In this mode for implementation, the joining is accomplished by inserting the nearer ends 3a of the four support wires 3 from the farther side in a second tubular piece 6 and fixing them within the second tubular piece 6 by welding, swaging or otherwise.

And each of the four support wires 3 extends radially toward the farther side and in the direction of the outer diameter.

Further, the filter body 4 consisting of the meshed material is formed into a meshed state by twining many filaments and into a basket shape whose face toward the nearer side is concave. Incidentally, it is not confined to a basket shape if the nearer side (the support wires 3 side or the principal wire 1 side) is concave and can capture embolic material. It is preferable, though, for the meshes of meshed material to become finer toward the central part of the concave.

The central convex side part (farther side part) of that filter body 4 is inserted into the nearer side part of a first tubular piece 5, and fixed within the first tubular piece 5 by welding, swaging or otherwise.

Further, the farther side ends of the four support wires 3 are made continuous from the nearer side end of the filter body 4 to integrate the four support wires 3 and the filter body 4.

And the tip of the principal wire 1 is inserted from the nearer side of the second tubular piece 6 and fixed to the second tubular piece 6.

Also, a guide wire 7 is inserted from the farther side of the first tubular piece 5 and fixed to the first tubular piece 5. Although this guide wire 7 also consists of steel filaments, it is more flexible in the radial direction than the principal wire 1. For this reason, even if the blood vessel is meandering, it can adequately guide the capture filter 2 along the blood vessel.

The filaments constituting the support wires 3 and the filter body 4 which make up the capture filter 2 in this mode for implementation consist of a superelastic alloy, which is a type of shape-memory alloy; by confining them in the aforementioned intended shape and subjecting them to heat treatment, for instance, at 500° C. for 40 minutes, they are caused to memorize that shape.

By being composed of such a super elastic alloy, the capture filter 2 is provided with an elastic force to form the shape.

Further in this mode for implementation, generation of a swelled part in the nodal portion between the support wires 3 and the filter body 4 is averted by integrating the filaments constituting the four support wires 3 and those constituting the filter body 4.

Figure 2:
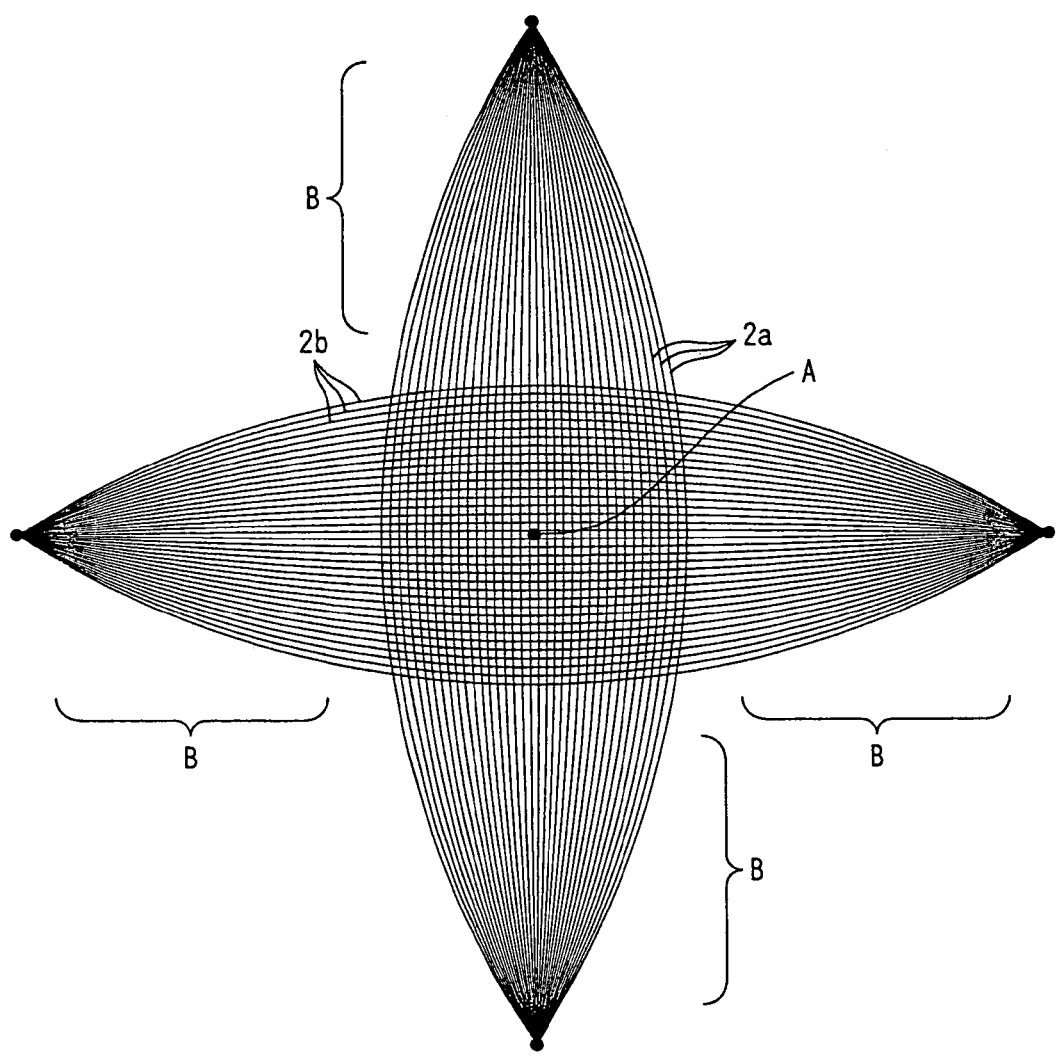
FIG. 2 is a drawing for describing an example fabrication of a capture filter pertaining to a mode for carrying out the invention.

To show an example of fabrication of the capture filter 2 by integrating the filaments constituting the four support wires 3 and those constituting the filter body 4 as stated above, a mesh is formed by so twining such filaments that 36 filaments 2a be arranged vertically and 36 filaments 2b arranged laterally as shown in FIG. 2 for instance; the central part A of the mesh is pulled backward as viewed in the drawing to form a basket-shaped concave to configure the filter body 4; and at the same time the respective ends of the four-filament sets (the part denoted by reference sign B in FIG. 2) are twined together to form the support wires 3.

Here, by pulling the central part A of the mesh to form the basket shape, a state in which the meshes are the finest in the central part of the concave, i.e. a state in which the meshes become finer as they approach the central part of the concave, is achieved.

Of course, the method of integrally fabricating the filaments constituting the four support wires 3 and those constituting the filter body 4 is not limited to this. For example, the concave of the filter body 4 can be formed by knitting filaments in a pipe shape as if to make a stocking, closing one of the open ends; at the same time the support wires 3 can be formed by dividing the filaments positioned at the other open end into sets of two each and twining them together. In this case, too, a meshed material whose meshes are the finest in the central part of the concave can be obtained by pulling one open end when it is to be closed.

To add, though it is preferable for the number of the support wires 3 to be three or more, two could also be acceptable.

Next, an example of use of the wire for intravital insertion will be described.

The wire for intravital insertion is inserted into a leading catheter 10 and, the state of the filter body 4 being held in the leading catheter 10 being kept as it is, the leading catheter 10 is injected into a blood vessel 11, which is a tract, and the tip of the leading catheter 10 is moved to the target position in the blood vessel, i.e. a lesioned position 12 (e.g. a stenosis region).

The filter body 4 here, in the state it is held in the leading catheter 10, is confined by the inner circumferential face of the leading catheter 10 to be folded to the size of the bore of the leading catheter 10.

Next, the filter body 4 is placed in the blood stream by so manipulating the principal wire 1 as to force the filter body 4 of the wire for insertion into intravital tracts out of the tip of the leading catheter 10 in the direction of the farther side (see FIG. 1). The filter body 4, once out of the leading catheter 10, is no longer confined by the leading catheter 10, swells out in the radial direction to automatically return to its original shape.

Next, after retreating the leading catheter 10 to before the stenosis region, the principal wire 1 is pulled back while applying a rotating action to the principal wire 1, and accumulated matter having built up in the blood vessel is scrapped off with the support wires 3. The scraped-off accumulated matter is collected into the concave of the filter body 4.

Then, upon completion of the collection, the leading catheter 10 and the filter body 4 are returned to inside a guide catheter not shown, and all of them are retreated in a state of being held in the guide catheter.

Incidentally, accumulated matter may as well be scraped off with another tool.

In the wire for insertion into intravital tracts, since the filter body 4 is configured of a mesh formed by twining filaments, the blood stream can be sufficiently ensured.

Herein, whereas the meshes of the filter body are the finest in the central part of the concave and more coarse toward the outer circumference, this gives a structure in which capturing begins in the central part of the concave and smooth flowing of the blood stream is facilitated by the coarse meshes toward the outer circumference, because the blood stream is the fastest in the central part of the blood vessel. Also, even if the mesh openings on the outer circumference side are somewhat greater in size than the target accumulated matter, the relative mesh openings in relative terms as viewed on a section orthogonal to the blood stream are fine enough to make capturing possible because scraping-off begins in the central part of the concave where the meshes are fine as stated above and the meshes are increasingly inclined toward the outer circumference in a lying posture relative to the blood current.

Also, by configuring the filaments of a superelastic alloy, they are enabled to automatically return to their original shape by merely drawing them out of the leading catheter 10, and therefore no separate mechanism is needed to cause the filter body 4 to swell out in the radial direction, and the capture filter 2 is enabled to be folded to a correspondingly smaller diameter.

Further, since the support wires 3 and the filter body 4 in a mesh state are configured of integrated filaments to allow no swollen nodal portion to be formed on the boundary between the support wires 3 and the filter body 4, the capture filter 2 is thereby enabled to be folded to a correspondingly smaller diameter.

As a result, it is made possible to insert the wire into a thinner blood vessel than a conventional such device can, and lesions in such thin blood vessels can be coped with.

Also, by disposing the more flexible guide wire 7 than the principal wire 1 on the farther side of the capture filter 2, the capture filter 2 is enabled to smoothly move, guided by the guide wire 7, even in a meandering blood vessel. The greater flexibility of the guide wire 7 than the principal wire 1 is intended to prevent the blood vessel wall from being damaged. The guide wire 7 can be dispensed with, though.

Also, by fixing the capture filter 2 to the principal wire 1 via the second tubular piece 6, splicing of the principal wire 1 to the capture filter 2 is facilitated.

Splicing between the capture filter 2 and the guide wire 7 is also facilitated by the intervening of the first tubular piece 5.

Although a case of configuring the support wires 3 and the filter body 4 of integrated filaments is illustrated here regarding the above described mode for implementation, it is also permissible to configure the support wires 3 and the filter body 4 of separate filaments and splicing the farther ends of the support wires 3 and the filter body 4 by welding or otherwise. However, the folded diameter will become thicker than in the foregoing embodiment by the thickness of the nodal portion, making the fabrication for manufacturing more troublesome. To add, if the linking positions between the individual support wires 3 and the filter body 4 are lagged in the axial direction of the principal wire 1 to prevent the nodal portions overlapping one another, the diameter can be set correspondingly smaller.

Also, though a case of configuring the filaments constituting the capture filter 2 of a superelastic alloy is illustrated here regarding the above described mode for implementation, they may also be composed of a shape-memory alloy which makes the temperature in the lesioned tract a transformation temperature. However, the use of a superelastic alloy makes the restoration of the original shape more certain when the filter is taken out of the leading catheter 10. Incidentally, a shape-memory resin may as well be used in place of a shape-memory alloy.

To add, it is not necessary to use a shape-memory alloy for all the filaments constituting the filter body 4, but some of the filaments which are twined may consist of another material. Even in this case, the shape-memory alloy part would exert elasticity to restore the original shape.

Also, the material for the filaments to constitute the capture filter 2 is not limited to a shape-memory alloy. For instance, they may be formed of a metal material, such as steel, and fabricated to provide elasticity of urging them in the direction of the intended shape. It is preferable for them to be formed of the shape-memory alloy, though, because they may not be restored when taken out of after a state of insertion in the leading catheter 10 for a long period.

Further, though the foregoing description referred to the blood vessel 11 as an example of intravital tract, the object is not limited to the blood vessel 11, but application to another intravital tract, such as the gall duct, is also possible. The invention excels in its applicability to small-diameter intravital tracts, though.

EMBODIMENT

An embodiment was configured of a capture filter 2 having a maximum expansible diameter of 8 mm and a filter body 4 consisting of 72 filaments. In this case, the diameter and mesh size of the expanded filter body 4 theoretically has a relationship shown in FIG. 3. The mesh opening sizes in the drawing are given in terms of diameters in the opening sectional areas converted into circular areas.

And a wire for intravital insertion equipped with the capture filter was arranged in a glass tube of 5.8 mm in bore, instead of a blood vessel, and a capture experiment was carried out. Incidentally, the maximum mesh size in this experiment was 0.25 mm.

And, while circulating water in the glass tube at a flow rate equivalent to the blood stream, polyvinyl alcohol (PVA) of 100 to 200 micrometers in grain size was let flow, and the weight of the PVA particles which were not captured and passed the filter was measured for evaluation.

As a result of the evaluation, it was confirmed that the capture filter had succeeded in capturing 95% of PVA. Thus, it is seen that sufficient capturing can be accomplished even if the meshes on the outer circumference are greater than the object to be captured.

INDUSTRIAL APPLICABILITY

As hitherto described, the wire for insertion into intravital tracts according to the present invention not only makes it possible to scrape off embolic material and the like while securing circulation within a tract, but also enables insertion into a tract of a thinner diameter, thereby enabling lesions in such thinner tracts to be treated.

The invention claimed is:

1. A wire for insertion into intravital tracts comprising:
a principal wire to be inserted into an intravital tract comprised of flexible filaments having at a tip a capture filter comprising:
a filter body formed into a mesh state by knitting ends of additional flexible filaments and forming the mesh state into a concave shape with a closed farther end and an opened nearer end; and
support wires formed by dividing the flexible filaments at the opened nearer end of the filter body into a plurality of sets, each set of flexible filaments twined together, wherein ends of the plurality of sets of filaments are spliced to the principal wire,
wherein each of the support wires extends radially in the direction toward the closed farther end and in the direction of an outer diameter, and the concave shape is configured to face the support wires and inclined toward an outer circumference of the filter body in a lying posture relative to the blood current, a mesh size of the mesh state decreases toward a central part of the concave shape at the farther closed end, and wherein
the filaments constituting the support wires and filter body are shape-memory alloy and have an elastic force to form the shape.

2. The wire for insertion into intravital tracts according to claim 1, wherein
the wire further comprises a guide wire joined to a convex side of the filter body and extending in the farther end direction.

3. The wire for insertion into intravital tracts according to claim 2, wherein
a central part of the filter body is joined to the nearer end side of a first tubular piece and fixed to the first tubular piece in a state in which the nearer end of the guide wire is inserted into the farther side of that first tubular piece.

4. The wire for insertion into intravital tracts according to claim 3, wherein
the nearer ends of the plurality of support wires are all fixed to a second tubular piece in a state in which they are inserted into the farther side of the second tabular piece, and fixed to the second tubular piece in a state in which the tip of the principal wire is inserted into the nearer side of the second tubular piece, and wherein an overall length of the capture filter between the first and second tubular pieces does not change when the outer diameter of the capture filter is reduced.

5. The wire for insertion into intravital tracts according to claim 1, wherein
the nearer ends of the plurality of support wires are all fixed to a second tubular piece in a state in which they are inserted into the farther side of the second tubular piece, and fixed to the second tubular piece in a state in which the tip of the principal wire is inserted into the nearer side of the second tubular piece.

6. The wire for insertion into intravital tracts according to claim 1, wherein the ends of the plurality of sets of filaments are spliced to the principal wire such that the ends of the plurality of sets of filaments do not move in relation to the principal wire, such that an overall length of the capture filter does not change when the outer diameter of the capture filter is reduced.

* * * * *